United States Patent
Almering et al.

(10) Patent No.: US 11,053,177 B2
(45) Date of Patent: Jul. 6, 2021

(54) PROCESS FOR THE PRODUCTION OF HIGH PURITY ISOBUTYLENE

(71) Applicant: LUMMUS TECHNOLOGY LLC, Bloomfield, NJ (US)

(72) Inventors: Martinus Johannes Almering, Houston, TX (US); Christopher Robbins, Pasadena, TX (US)

(73) Assignee: LUMMUS TECHNOLOGY LLC, Bloomfield, NJ (US)

( * ) Notice: Subject to any disclaimer, the term of this patent is extended or adjusted under 35 U.S.C. 154(b) by 0 days.

(21) Appl. No.: 16/549,804

(22) Filed: Aug. 23, 2019

(65) Prior Publication Data

US 2020/0062676 A1  Feb. 27, 2020

Related U.S. Application Data

(60) Provisional application No. 62/722,023, filed on Aug. 23, 2018.

(51) Int. Cl.
| | |
|---|---|
| *C07C 5/25* | (2006.01) |
| *B01D 3/00* | (2006.01) |
| *C07C 7/00* | (2006.01) |
| *C07C 7/04* | (2006.01) |
| *B01D 3/42* | (2006.01) |
| *B01J 8/00* | (2006.01) |

(52) U.S. Cl.
CPC ............ *C07C 5/2506* (2013.01); *B01D 3/009* (2013.01); *B01D 3/4227* (2013.01); *B01J 8/001* (2013.01); *C07C 7/005* (2013.01); *C07C 7/04* (2013.01); *B01J 2208/00176* (2013.01)

(58) Field of Classification Search
CPC ...................................................... B01D 3/009
See application file for complete search history.

(56) References Cited

U.S. PATENT DOCUMENTS

| | | |
|---|---|---|
| 4,242,530 A | 12/1980 | Smith, Jr. |
| 4,443,559 A | 4/1984 | Smith, Jr. |
| 4,731,229 A | 3/1988 | Sperandio |

(Continued)

OTHER PUBLICATIONS

International Search Report and Written Opinion issued in corresponding International Application No. PCT/US2019/047896 dated Dec. 13, 2019 (10 pages).

*Primary Examiner* — Philip Y Louie
*Assistant Examiner* — Alyssa L Cepluch
(74) *Attorney, Agent, or Firm* — Osha Bergman Watanabe & Burton LLP

(57) ABSTRACT

Processes for the production of high purity isobutylene are disclosed. The processes may include supplying a mixed C4 feed stream to a catalytic distillation column, which may contain a butene isomerization catalyst. 1-butene is isomerized to 2-butene and concurrently in the catalytic distillation column the 2-butene is separated from the isobutane and isobutylene. The overheads fraction comprising the isobutane and isobutylene is then condensed in an overheads system and fed to a splitter, where the isobutane is separated from the isobutylene. The process further includes operating the catalytic distillation column at an overheads temperature greater than a bottoms temperature of the splitter, and heating a portion of the splitter bottoms stream via indirect heat exchange with at least a portion of the catalytic distillation column overheads fraction, thereby producing a heated bottoms stream (reboil vapor) fed to the splitter and a cooled overheads fraction.

10 Claims, 2 Drawing Sheets

(56) References Cited

U.S. PATENT DOCUMENTS

| | | |
|---|---|---|
| 5,073,236 A | 12/1991 | Gelbein et al. |
| 5,189,001 A | 2/1993 | Johnson |
| 5,266,546 A | 11/1993 | Hearn |
| 5,348,710 A | 9/1994 | Johnson et al. |
| 5,431,890 A | 7/1995 | Crossland et al. |
| 5,730,843 A | 3/1998 | Groten et al. |
| 6,242,661 B1 | 6/2001 | Podrebarac et al. |
| 2010/0197987 A1 | 8/2010 | Almering |

PROCESS FOR THE PRODUCTION OF HIGH PURITY ISOBUTYLENE

FIELD OF THE DISCLOSURE

Embodiments herein relate to the production of a high purity isobutylene product from mixed hydrocarbon streams containing isobutylene, isobutane, and 1-butene.

BACKGROUND

Isobutylene is present in mixed hydrocarbon streams that include saturated and unsaturated C4 hydrocarbon streams. Unfortunately, the boiling point difference between isobutylene and 1-butene is too small for distillation to be an effective means for recovering high purity isobutylene.

One process for producing high purity isobutylene from mixed C4 fractions is via back-cracking of methyl tertiary butyl ether (MTBE), such as described in U.S. Pat. No. 7,968,758. The isobutylene in the mixed butenes stream may be reacted with an alcohol, such as methanol, to form MTBE. After separation from the normal butenes, the MTBE may be dissociated to form isobutylene and methanol, allowing recovery of a high purity isobutylene stream. This process, however, involves many unit operations and frequent catalyst replacement.

U.S. Pat. No. 6,242,661 describes a process for the separation of isobutylene, otherwise inseparable from butene-1 by fractionation, in high purity. As described therein, the isobutylene is separated from butenes contained in a mixed hydrocarbon stream containing butene-1, butene-2 and small amounts of butadiene. The mixed hydrocarbon stream is fed to a distillation column reactor containing an alumina supported palladium oxide catalyst. The column is operated to tend to exclude butene-2 from contact with the catalyst and to maintain butene-1 in contact with the catalyst to isomerize the butene-1 to butene-2. As butene-2 is produced, it is distilled away from the catalyst, upsetting the equilibrium and allowing for a greater than equilibrium amount of butene-2. The isobutylene and isobutane are concurrently separated from the butene-2. Additionally, any butadiene in the feed may be hydrogenated to butenes. The bottoms is rich in butene-2, while the overheads, including isobutylene and isobutane, may be fed to a splitter for separation of the isobutylene from the isobutane.

SUMMARY

A more cost effective and operating efficient process for the production of a high purity isobutylene stream has now been developed. Processes according to embodiments herein include a catalytic distillation step and a fractionation step. In the catalytic distillation step, a stream containing mixed C4s is fed to a catalytic distillation column, in which the combined distillation and linear hydroisomerization of 1-butene to 2-butene allows for the complete separation of all other C4 components, recovered as a bottoms stream along with the 2-butenes, from an overhead stream including isobutane and isobutylene. The overhead stream may then be fed to a fractionation column to separate and recover a high purity isobutylene bottoms stream and an isobutane overheads stream.

The catalytic distillation column may be operated at an elevated pressure and temperature, where the overheads temperature of the catalytic distillation column is greater than the bottoms temperature of the isobutane-isobutylene fractionation column. This allows overhead condensing heat to be used to provide heat to the reboiler of the fractionation column, which may be operating at lower pressures and temperatures, allowing the isobutane-isobutylene column overheads system to operate with cooling water.

In one aspect, embodiments herein are directed toward processes for the production of high purity isobutylene. The processes may include supplying a mixed C4 feed stream, including isobutylene, isobutane, and 1-butene, and optionally one or more of butadiene, 2-butene, or n-butanes, to a catalytic distillation column. The catalytic distillation column may include one or more catalytic distillation zones containing a butene isomerization catalyst. In the catalytic distillation column, the process concurrently isomerizes 1-butene to 2-butene and separates the 2-butene from the isobutane and isobutylene. The 2-butene is recovered from the catalytic distillation column as a bottoms stream, and overheads fraction comprising the isobutane and isobutylene is recovered from the catalytic distillation column. The overheads fraction comprising the isobutane and isobutylene is then condensed in an overheads system. At least a portion of the condensed overheads fraction is fed to a splitter. In the splitter (fractionation column), the isobutane is separated from the isobutylene, thereby recovering a bottoms stream from the splitter including the isobutylene, which may be at high purity, and an overheads stream including the isobutane. The process further includes operating the catalytic distillation column at an overheads temperature greater than a bottoms temperature of the splitter, and heating a portion of the splitter bottoms stream via indirect heat exchange with at least a portion of the catalytic distillation column overheads fraction, thereby producing a heated bottoms stream fed to a lower portion of the splitter and a cooled overheads fraction. The cooled overheads stream may then be fed via at least one flow line to the catalytic distillation column overheads system.

In some embodiments, the cooled overheads may be partially condensed during heat exchange in the splitter reboiler. An accumulator may be provided for receiving the cooled overheads stream from the splitter reboiler. A first flow line and a second flow line may be provided to then feed the partially condensed stream to the overheads system, including: feeding a vapor portion of the cooled overhead stream via the first flow line from the accumulator to the overheads system; and feeding a liquid portion of the cooled overhead stream via the second flow line from the accumulator to the overheads system.

In one aspect, embodiments herein are directed toward processes for the production of high purity isobutylene. The processes may include supplying a mixed C4 feed stream, including isobutylene, isobutane, and 1-butene, and optionally one or more of butadiene, 2-butene, or n-butanes, to a catalytic distillation column. The catalytic distillation column may include one or more catalytic distillation zones containing a butene isomerization catalyst. In the catalytic distillation column, the process concurrently isomerizes 1-butene to 2-butene and separates the 2-butene from the isobutane and isobutylene. The 2-butene is recovered from the catalytic distillation column as a bottoms stream, and overheads fraction comprising the isobutane and isobutylene is recovered from the catalytic distillation column. The overheads fraction comprising the isobutane and isobutylene is then condensed in an overheads system. At least a portion of the condensed overheads fraction is fed to a splitter. In the splitter (fractionation column), the isobutane is separated from the isobutylene, thereby recovering a bottoms stream from the splitter including the isobutylene, which may be at high purity, and an overheads stream including the isobutane. The process further includes operating the catalytic distillation column at an overheads temperature or greater than 60° C., and operating the splitter at a bottoms temperature of less than 55° C. A portion of the splitter bottoms stream may be heated via indirect heat exchange with at least a portion of the catalytic distillation column overheads fraction, producing a heated bottoms stream fed to a lower portion of the splitter and a cooled overheads fraction, which may be fed to the overheads system. In some embodiments, the catalytic distillation column may be operated at an overheads temperature or greater than 85° C.

In another aspect, embodiments herein are directed toward a system for the production of high purity isobutylene. The system may include a feed stream for supplying a mixed C4 stream comprising isobutylene, isobutane, and 1-butene, and optionally comprising one or more of butadiene, 2-butene, or n-butanes. The feed stream may supply the hydrocarbons to a catalytic distillation column containing a butene isomerization catalyst, where the catalytic distillation column may be configured to operate at a temperature of greater than 85° C., for example, and to concurrently isomerize 1-butene to 2-butene and separate the 2-butene from the isobutane and isobutylene. A bottoms stream may be provided for recovering the 2-butene from the catalytic distillation column, and an overheads stream may be provided for recovering an overheads fraction comprising the isobutane and isobutylene from the catalytic distillation column. An overheads system may provide for condensing the overheads fraction comprising the isobutane and isobutylene, at least a portion of which may be provided to a splitter for separating the isobutane from the isobutylene. In some embodiments, the system is configured to operate with a catalytic distillation column overheads temperature greater than a bottoms temperature of the splitter. A splitter reboiler may be configured to heat a portion of the isobutylene bottoms via indirect heat exchange with at least a portion of the overheads stream, producing a heated bottoms stream fed to a lower portion of the splitter and a partially condensed overheads stream, which may be fed to the catalytic distillation column overhead system.

DETAILED DESCRIPTION

Figure 1:
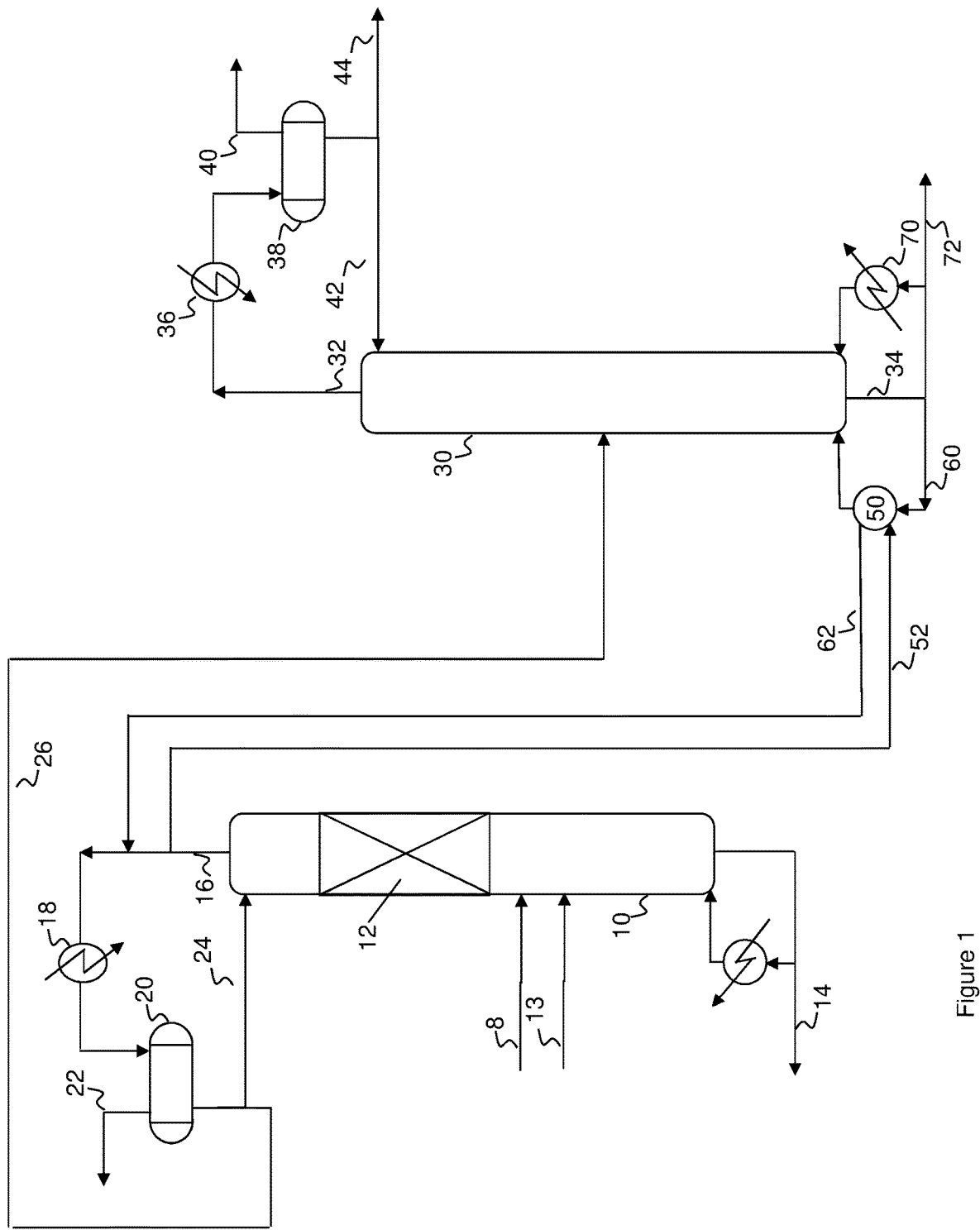
FIG. 1 is a simplified process flow diagram of a system for producing high purity isobutylene according to embodiments herein.

Embodiments herein relate to a process for the production of High Purity Isobutylene (HPIB) through a heat integrated catalytic distillation process.

A first step in the process involves a catalytic distillation process to separate a stream containing isobutylene and isobutane from a stream containing mixed C4s, which may include 1-butene, 2-butenes, isobutane, isobutylene, butadienes, and n-butanes. The catalytic distillation combines distillation and linear hydroisomerization of 1-butene to 2-butenes, and allows for the complete separation of all heavier (higher boiling) C4 components out of the overhead isobutane plus isobutylene stream. This stream is then fed to a second step in the process, which includes a fractionation column to separate a high purity (98.0-99.99 wt %) isobutylene from the isobutane.

The catalytic distillation process is operated at an elevated pressure, much above the normal pressure as disclosed in U.S. Pat. No. 6,242,661, for example, where the "normal" pressure is just high enough for cooling water or air cooled condensing of the overheads. In contrast, the catalytic distillation process in embodiments herein operates at an elevated pressure, so as to cause a higher condensing temperature and to allow the overhead condensing heat to be used to provide heat to the reboiler in the isobutane-isobutylene fractionation column, which may operate at a lower pressure. The isobutane-isobutylene fractionator overhead vapor may be condensed with cooling water.

It was unexpected that the catalytic distillation column can operate at the higher operating pressure and perform well enough to generate the high purity isobutylene and isobutane streams.

Embodiments herein may provide for a lower cost HPIB Process, and may be used to revamp existing catalytic distillation units for producing isobutylene, such as CDDeIB Units (Lummus Technology LLC, Houston, Tex.), for example. HPIB through the process of embodiments herein involves only two main fractionation units, resulting in a low capital expenditure (low CAPEX), and with the heat integration it is also a low operating expense (OPEX) operation. Further, embodiments herein may require less frequent catalyst replacement as compared to the lower temperature, lower pressure operations. These benefits may be attributed to the much higher operating pressure of the catalytic distillation reactor, which makes the heat integration feasible. One skilled in the art, would not normally operate a distillation column at a higher pressure than necessary for condensing with a readily available low cost cooling medium such as air or cooling water. However, the reaction benefits and cost benefits found at the higher operating temperatures according to embodiments herein clearly outweigh the typical inclination to operate at lower pressures.

A typical mixed C4 stream to be separated according to embodimeents herein may contain the following components, with the table including their corresponding boiling points.

| Component | Normal Boiling Point (° C.) |
| --- | --- |
| Isobutane | −11.7 |
| Isobutylene | −6.9 |
| Butene-1 | −6.3 |
| 1,3-Butadiene | −4.4 |
| n-Butane | −0.5 |
| trans-butene-2 | 1.0 |
| cis-butene-2 | 3.7 |

The closeness of the boiling points of butene-1 and isobutylene make the separation of butene-1 from isobutylene difficult by distillation. However, the boiling point of butene-2 is about 8 degrees higher for the trans isomer and more than 10 degrees higher for the cis isomer. Therefore, as the butene-1 is isomerized to butene-2, the normal butenes (as butene-2) can be more readily separated from the isobutylene and isobutane.

The isomerization reaction is reversible as may be noted by references to "equilibrium" concentration in fixed bed reactors for a given residence time. In a catalytic distillation, the catalyst serves as a distillation component, the equilibrium is constantly disturbed, and thus the removal of butene-2 as a bottoms product constantly drives the reaction to increase production of butene-2. The catalytic material is a component of a distillation system functioning as both a catalyst and distillation packing, a packing for a distillation column having both a distillation function and a catalytic function. The reaction system can be described as heterogeneous as the catalyst remains a distinct entity.

The catalytic material employed for the isomerization reaction is preferably in a form to serve as distillation packing in such conventional distillation packing shapes as Raschig rings, Pall rings, saddles or the like and as such other structures as, for example, balls, irregular, sheets, tubes, spirals, packed in bags or other structures (such as those described in U.S. Pat. Nos. 4,242,530, 4,443,559, 5,189,001, 5,348,710, and 5,431,890), plated on grills or screens, or reticulated polymer foams (the cellular structure of the foams must be sufficiently large so as to not cause high pressure drops through the column, or otherwise arranged such as in chunks or concentration tubes to allow vapor flow). Similarly, the catalyst may be employed as palladium oxide supported on one-eighth inch alumina extrudates, either in bags or loosely packed in the column. In some embodiments, the catalyst may be contained in a structure as disclosed in U.S. Pat. Nos. 5,730,843, 5,266,546, 4,731,229, and 5,073,236.

Embodiments herein may perform the catalytic distillation step in a catalyst packed column which can be appreciated to contain a vapor phase and some liquid phase, as in any distillation. Because the reaction is occurring concurrently with distillation, the initial reaction products are removed from the reaction zone as quickly as possible. Further, as all the components are boiling, the temperature of reaction is controlled by the boiling point of the mixture at the system pressure, which may vary from tray to tray. The heat of reaction simply creates more boil up but no increase in temperature. Additionally, the reaction has an increased driving force because the reaction products have been removed and cannot contribute to a reverse reaction. As a result, a great deal of control over the rate of reaction and distribution of products can be achieved by regulating the system pressure. Also, adjusting the throughput (residence time=liquid hourly space velocity$^{-1}$) gives further control of product distribution and degree of butene-1 to butene-2 conversion.

The temperature in the distillation column reactor is determined by the boiling point of the liquid mixture present at any given pressure. The temperature in the lower portions of the column will reflect the constitution of the material in that part of the column, and will be a higher temperature than the overhead; that is, at constant pressure a change in the temperature of the system indicates a change in the composition in the column. To change the temperature, the pressure is changed. Temperature control in the reaction zone is thus effected by a change in pressure; by increasing the pressure, the temperature in the system is increased, and vice versa.

The catalytic distillation column according to embodiments herein may be operated at an overhead temperature in the range of 42° C. to 138° C. and at pressures in the range of 5 bara to 20 bara, bearing in mind the effect of pressure on temperature as discussed above. In other embodiments, the catalytic distillation column according to embodiments herein may be operated at an overhead temperature in the range of 85° C. or 90° C. to 130° C. or 135° C. and at pressures in the range of 9 bara, 10 bara, or 11 bara to 16 bara, 18 bara, or 20 bara, where any lower limit may be combined with any upper limit. In other embodiments, the overhead temperature of the catalytic distillation column may be in the range from 42° C. to about 80° C., such as from about 47° C. to about 68° C., or from about 60° C. to about 65° C. In yet other embodiments, the overhead temperature may be in the range from a lower limit of 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 85 or 90° C. to an upper limit of 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 85, 90, 100, 110, 120, 130, or 138° C., where any lower limit may be combined with any upper limit. In some embodiments, the overhead pressure of the catalytic distillation column may be in the range from about 5 bara to about 12 bara, such as in the range from about 7 bara to about 10 bara. In yet other embodiments, the overhead pressure of the catalytic distillation column may be in the range from a lower limit of about 9, 10, 11, 12, 13, 14, or 15 bara to an upper limit of about 14, 15, 16, 17, 18, 19, or 20 bara. Bottoms temperatures of the catalytic distillation column will correspond to the boiling point of the higher boiling components at the operating conditions, and in various embodiments, may be in the range from about 60° C. to about 180° C., such as from about 60° C. to about 100° C., or from about 65° C. to about 88° C., for example, but may also be higher based on the desired overhead temperature and pressure. The temperature of operation may also take into consideration the activity of the catalyst for promoting the desired 1-butene to 2-butene reaction.

In embodiments herein, the catalytic distillation column is operated under conditions, particularly temperature and pressure, which tend to exclude butene-2 from contact with the catalyst while holding the butene-1 in contact with the catalyst. Thus, as butene-1 is isomerized to butene-2, it drops down in the column away from the catalyst and is removed as bottoms. The column may include a reflux, where the reflux ratio may be in the range from 0.5:1 to 33:1, for example.

The catalyst contained in the reaction zone of the catalytic distillation column may be any catalyst suitable for the isomerization or hydroisomerization of 1-butene to 2-butene. In some embodiments, the catalyst may contain palladium, and may be in the form of an extrudate, for example. For hydroisomerization, the hydrogen rate to the distillation column reactor should be sufficient to maintain the catalyst in the active (hydride) form, as hydrogen is lost from the catalyst by hydrogenation when butadiene is contained in the feed. The hydrogen rate may be adjusted such that there is sufficient hydrogen to support the butadiene hydrogenation reaction and replace hydrogen lost from the catalyst but kept below that required for hydrogenation of butenes or to cause flooding of the column. Generally, the mole ratio of hydrogen to C4 hydrocarbon fed to the bed of catalytic distillation column will be in the range from about 0.01:1 to 0.60:1, preferably 0.01:1 to 0.10:1.

The hydrocarbon stream fed to the system may be selected as one which is high in $C_4$'s, especially normal butenes and isobutylene. Saturated $C_4$'s only contribute to the vapor loading in the column. High concentrations of butadiene are not necessarily desired as it has been found that the isomerization reaction does not proceed until near completion of the butadiene hydrogenation reaction. A practical limit to butadiene is thus established by the distillation column reactor bed size and reaction time available for the hydrogenation and isomerization reactions. Additionally, the butadiene can be extracted to practical limits before feeding to the catalytic distillation column due to its economic value. A typical candidate stream is the mixed $C_4$ stream from a fluid catalytic cracking unit (FCCU) or a mixed C4 raffinate stream from a butadiene extraction unit fed with steam cracker C4's, for example.

Referring now to FIG. 1, a simplified process flow diagram of HPIB production processes according to embodiments herein is illustrated. The initial step is feeding a mixed $C_4$ stream 8, such as from a butadiene extraction plant or a FCCU, to a catalytic distillation column 10. In the catalytic distillation column 10, the mixed $C_4$ stream containing butene-1, isobutylene and isobutylene, among other C4 components, is fed to catalytic distillation column 10 near the bottom of a catalytic distillation section 12 (catalyst zone 12), which contains the supported hydroisomerization catalyst in the form of a catalytic distillation structure. Hydrogen may be fed via flow line 13, also introduced below the catalyst zone 12.

As the reactant feed contacts the catalyst, any butadiene in the feed is hydrogenated to butenes and equilibrium amounts of butene-1 and butene-2 are produced at the catalyst. The butene-2 is immediately distilled away and taken as bottoms, driving the reaction at the catalyst sites toward the production of butene-2.

The stripping section of the column may contain a conventional distillation structure, such as bubble cap, sieve trays or inert packing to allow for complete separation of the butene-2 product from the lower boiling isobutylene and isobutane. Any normal butane will also be removed as bottoms. The butene-2 and normal butane may then be recovered from the catalytic distillation column 10 via flow line 14.

Overhead stream 16, comprising isobutylene and isobutane is condensed in condenser 18. The condensed overheads are collected in receiver separator 20, wherein the liquid isobutylene and isobutane are separated from hydrogen and light materials which are vented via flow line 22. The hydrogen may be recycled to the distillation column reactor if desired (not shown). A portion of the condensed overhead product is recycled via flow line 24 to the distillation column reactor 10 as reflux. The isobutylene and isobutane are removed as overheads product via flow line 26, which is passed on to a splitter 30 for separation of the isobutylene from the isobutane.

In splitter 30, the isobutane and the isobutylene are separated via conventional distillation. Typical splitter 30 operating conditions may include an overhead temperature in the range from 22° C. to 55° C., such as from about 37° C. to about 45° C., and overhead pressures in the range from about 3 bara to about 7 bara, such as from about 5 bara to about 6 bara. Bottoms temperatures in the splitter may range from about 35° C. to about 65° C., such as from about 50° C. to about 60° C. Splitter 30 may contain enough trays to effect the desired separation, allowing a recovery of an on overhead fraction 32 containing isobutane and a bottoms fraction 34 containing isobutylene.

The overheads 32 may be condensed in a condenser 36 and collected in a receiver separator 38. Overheads 32 may contain primarily isobutane, but may contain some isobutylene and other light components. Components lighter than isobutane, if present, may be vented via flow line 40. A portion of the condensed overhead product collected in receiver separator 38 may be recycled via flow line 42 to splitter 30 as a reflux. The isobutane may be recovered as an overheads product via flow line 44.

In embodiments herein, the overhead temperature of catalytic distillation column 10 is maintained at a higher temperature than the bottoms temperature of distillation column 30. Heat may thus be supplied to splitter 30 reboiler 50 via indirect heat exchange with overhead stream 16. A flow line 52 may be used to route all or a portion of overhead stream 16 to reboiler 50, cooling and in some embodiments partially condensing the overhead components in stream 52 via indirect heat exchange with a portion 60 of bottoms stream 34. The resulting cooled overhead stream(s) 62 may then be returned to condenser 18 and/or receiver 20 for further condensation, cooling, and recovery, as described above.

Additional heat may be supplied, as necessary, to the bottoms of splitter 30 by an additional reboiler 70. Reboiler 70 may be used to heat a second portion of bottoms stream 34, for example, via indirect heat exchange with all or a portion of the distillation column bottoms stream 14, the cooled heat exchange medium 80 resulting from catalytic distillation column reboiler 82, or other available heat sources. A bottoms product, comprising high purity isobutylene, may be recovered via flow line 72.

Figure 2:
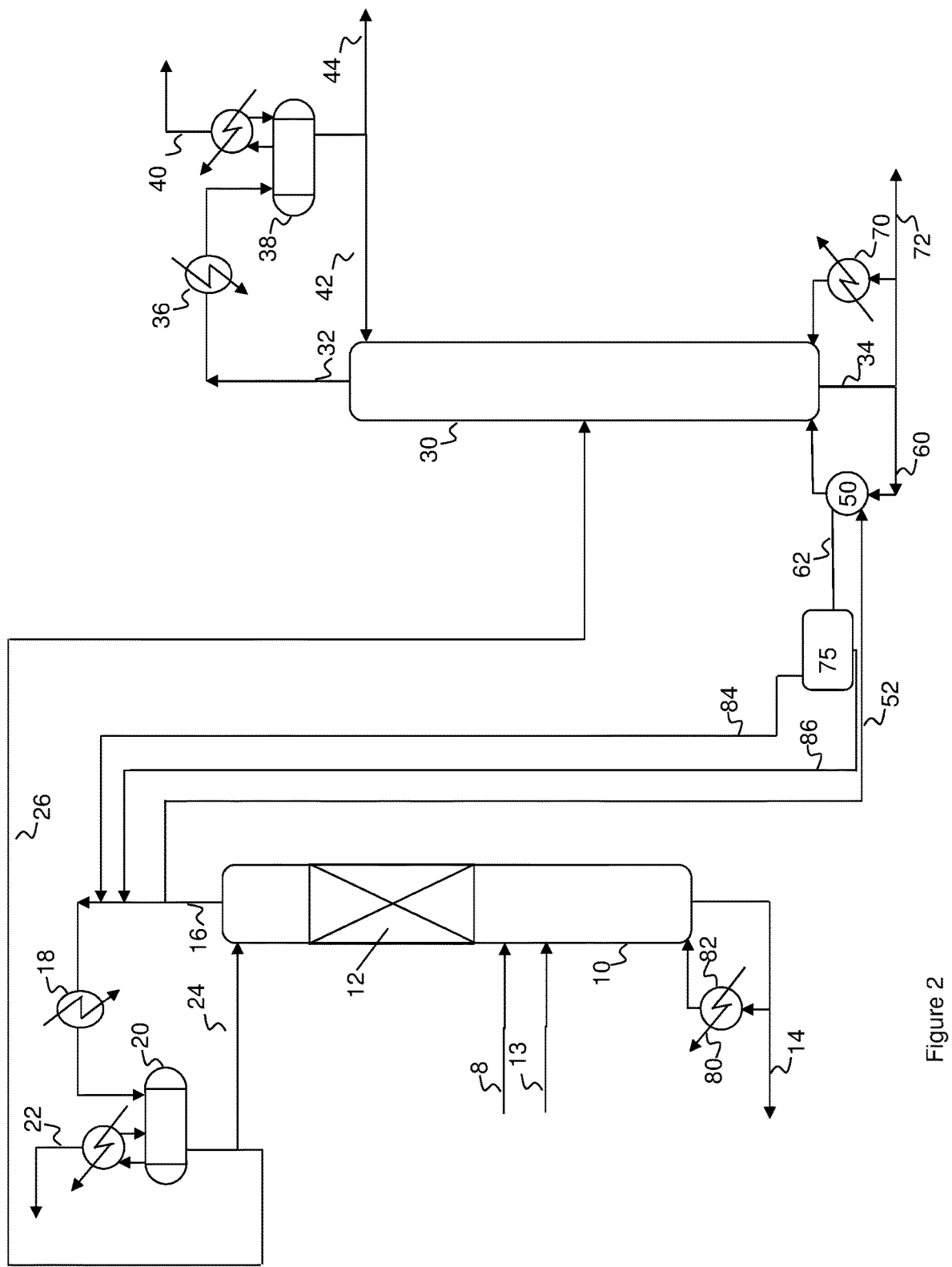
FIG. 2 is a simplified process flow diagram of a system for producing high purity isobutylene according to embodiments herein.

FIG. 2 illustrates a flow diagram of another system according to embodiments herein. FIG. 2 illustrates additional heat exchangers, collectors, and flow streams that may be used to facilitate the production of a high purity isobutylene stream according to embodiments herein.

As illustrated in FIG. 2, the system may further include an accumulator 75 for receiving the cooled overheads stream 62, which may be partially condensed via heat exchange with the splitter column bottoms 60 in reboiler 50. The system may also include a first flow line and a second flow line for feeding of the cooled overheads from accumulator 75 to the overhead system. A first flow line 84 may be provided for feeding a vapor portion of the cooled overhead stream from the accumulator to the overheads system. And, a second flow line 86 may be provided for feeding a liquid portion of the cooled overhead stream from the accumulator 75 to the overheads system.

As described above, embodiments herein provide for the production of high purity isobutylene. Advantageously, embodiments herein utilize a higher than necessary pressure in the catalytic distillation column, allowing heat integration and improved separations, where the process may have low capital and operating expenses. While the high operating pressures in the catalytic distillation column make the heat integration feasible, it has also been found that the catalytic distillation column may operate efficiently at the higher temperatures, providing for less frequent catalyst changes, especially compared to MTBE back-cracking. Such may provide for a lower capital and operating cost process to produce high purity isobutylene.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the production of high purity isobutylene, comprising:
   supplying a mixed C4 feed stream, comprising isobutylene, isobutane, and 1-butene, and optionally comprising one or more of butadiene, 2-butene, or n-butanes, to a catalytic distillation column containing a butene isomerization catalyst;
   in the catalytic distillation column, concurrently isomerizing 1-butene to 2-butene and separating the 2-butene from the isobutane and isobutylene;
   recovering the 2-butene from the catalytic distillation column as a bottoms stream;
   recovering an overheads fraction comprising the isobutane and isobutylene from the catalytic distillation column;

condensing the overheads fraction comprising the isobutane and isobutylene in an overheads system comprising at least one condenser;

feeding at least a portion of the condensed overheads fraction to a splitter and separating the isobutane from the isobutylene in the splitter;

recovering a bottoms stream from the splitter comprising the isobutylene; and recovering an overheads stream from the splitter comprising the isobutane;

wherein the process further comprises:

operating the catalytic distillation column at an overheads temperature greater than a bottoms temperature of the splitter; and heating a portion of the splitter bottoms stream via indirect heat exchange with at least a portion of the catalytic distillation column overheads fraction, producing a heated bottoms stream fed to a lower portion of the splitter and a cooled overheads fraction; and feeding the cooled overheads stream via at least one flow line to the overheads system.

2. The process of claim 1, further comprising an accumulator for receiving the cooled overheads stream, and wherein the at least one flow line for feeding the cooled overheads stream to the overheads system comprises a first flow line and a second flow line, the process further comprising:

feeding a vapor portion of the cooled overhead stream via the first flow line from the accumulator to the overheads system; and feeding a liquid portion of the cooled overhead stream via the second flow line from the accumulator to the overheads system.

3. The process of claim 1, further comprising:

heating a second portion of the splitter bottoms stream via indirect heat exchange with at least a portion of the catalytic distillation column bottoms fraction, producing a heated splitter bottoms stream fed to a lower portion of the splitter and a cooled 2-butene fraction.

4. The process of claim 1, wherein the catalytic distillation column is operated at an overheads temperature in the range from about 42° C. to about 138° C.

5. The process of claim 1, wherein the catalytic distillation column is operated at an overheads temperature in the range from about 85° C. to about 138° C.

6. The process of claim 1, wherein the catalytic distillation column is operated at an overheads temperature in the range from about 60° C. to about 65° C.

7. A process for the production of high purity isobutylene, comprising:

supplying a mixed C4 feed stream, comprising isobutylene, isobutane, and 1-butene, and optionally comprising one or more of butadiene, 2-butene, or n-butanes, to a catalytic distillation column containing a butene isomerization catalyst;

in the catalytic distillation column, concurrently isomerizing 1-butene to 2-butene and separating the 2-butene from the isobutane and isobutylene;

recovering the 2-butene from the catalytic distillation column as a bottoms stream;

recovering an overheads fraction comprising the isobutane and isobutylene from the catalytic distillation column;

condensing the overheads fraction comprising the isobutane and isobutylene in an overheads system comprising at least one condenser;

feeding at least a portion of the condensed overheads fraction to a splitter and separating the isobutane from the isobutylene in the splitter;

recovering a bottoms stream from the splitter comprising the isobutylene; and recovering an overheads stream from the splitter comprising the isobutane;

wherein the process further comprises:

operating the catalytic distillation column at an overheads temperature of greater than 60° C.;

operating the splitter at a bottoms temperature of less than 55° C.; and heating a portion of the splitter bottoms stream via indirect heat exchange with at least a portion of the catalytic distillation column overheads fraction, producing a heated bottoms stream fed to a lower portion of the splitter and a cooled overheads fraction; and feeding the cooled overheads stream via at least one flow line to the overheads system.

8. The process of claim 7, further comprising an accumulator for receiving the cooled overheads stream, and wherein the at least one flow line for feeding the cooled overheads stream to the overheads system comprises a first flow line and a second flow line, the process further comprising:

feeding a vapor portion of the cooled overhead stream via the first flow line from the accumulator to the overheads system; and feeding a liquid portion of the cooled overhead stream via the second flow line from the accumulator to the overheads system.

9. The process of claim 7, further comprising:

heating a second portion of the splitter bottoms stream via indirect heat exchange with at least a portion of the catalytic distillation column bottoms fraction, producing a heated splitter bottoms stream fed to a lower portion of the splitter and a cooled 2-butene fraction.

10. The process of claim 7, wherein the catalytic distillation column is operated at an overheads temperature of greater than 85° C.

* * * * *